(12) United States Patent
Ito et al.

(10) Patent No.: US 8,236,923 B2
(45) Date of Patent: *Aug. 7, 2012

(54) FLUORINE-CONTAINING POLYMER AND METHOD OF PRODUCING FLUORINE-CONTAINING POLYMER

(75) Inventors: Takayuki Ito, Minami-ashigara (JP); Toshimitsu Sakuma, Minami-ashigara (JP); Masayuki Harada, Minami-ashigara (JP)

(73) Assignee: Fujifilm Corporation, Tokyo (JP)

( * ) Notice: Subject to any disclaimer, the term of this patent is extended or adjusted under 35 U.S.C. 154(b) by 456 days.

This patent is subject to a terminal disclaimer.

(21) Appl. No.: 12/520,366

(22) PCT Filed: Jan. 15, 2008

(86) PCT No.: PCT/JP2008/050374
§ 371 (c)(1),
(2), (4) Date: Jun. 19, 2009

(87) PCT Pub. No.: WO2008/087946
PCT Pub. Date: Jul. 24, 2008

(65) Prior Publication Data
US 2009/0318650 A1 Dec. 24, 2009

(30) Foreign Application Priority Data

Jan. 16, 2007 (JP) ................. 2007-007514

(51) Int. Cl.
*C08G 63/68* (2006.01)
*C08G 75/04* (2006.01)
(52) U.S. Cl. ........ 528/364; 528/376; 528/392; 528/401; 528/402; 528/405; 528/406; 528/425
(58) Field of Classification Search .............. 528/364, 528/376, 392, 393, 401, 402, 405, 406, 425
See application file for complete search history.

(56) References Cited

U.S. PATENT DOCUMENTS

| | | | |
|---|---|---|---|
| 3,391,118 A | 7/1968 | Cook | |
| 5,013,821 A * | 5/1991 | Heller et al. | 528/376 |
| 5,364,547 A | 11/1994 | Babb et al. | |
| 5,942,572 A | 8/1999 | Chittofrati et al. | |
| 7,875,697 B2 * | 1/2011 | Alkatout et al. | 528/392 |
| 8,119,765 B2 * | 2/2012 | Ito | 528/402 |

FOREIGN PATENT DOCUMENTS

| | | |
|---|---|---|
| JP | 4-325237 A | 11/1992 |
| JP | 10-101922 A | 4/1998 |
| JP | 10-251353 A | 9/1998 |
| JP | 2006-154590 A | 6/2006 |
| WO | WO-2007/043672 A1 | 4/2007 |

OTHER PUBLICATIONS

Grob et al., Journal of Fluorine Chemistry, 26 (1984), pp. 457-465.
Iacono et al., "Facile preparation of fluorovinylene aryl ether telechelic polymers with dual functionality for thermal chain extension and tandem crosslinking", Chemical Communications, 2006, vol. 46, pp. 4844-4846.
Moldavskii et al., "Polyfluorinated organic compounds Reaction of polyhydric alcohols with some internal perfluoroolefins" Zhurnal Obshchei Khimii, 1996, vol. 66, No. 12, pp. 1995-2002.

* cited by examiner

*Primary Examiner* — Mark Eashoo
*Assistant Examiner* — Nicole M Buie-Hatcher
(74) *Attorney, Agent, or Firm* — Birch, Stewart, Kolasch & Birch, LLP

(57) ABSTRACT

A method of producing a fluorine-containing polymer, containing conducting an addition polymerization of a fluorine-containing compound having 2 or more terminal fluorine-containing vinyl groups each directly bonded to an oxygen atom per molecule, and a compound having 2 or more groups represented by —XH, where X represents an oxygen atom or a sulfur atom; and a fluorine-containing polymer comprising a repeating unit represented by formula (i):

$$\left( \begin{array}{c} H \\ \diagdown \\ C \\ F_2 \end{array} \begin{array}{c} O \\ \diagup \diagdown \\ Rf_2 \end{array} \begin{array}{c} Rf_1 \\ \\ Rf_3 \end{array} \begin{array}{c} O \\ \diagdown \diagup \\ \end{array} \begin{array}{c} H \\ \diagup \\ C \\ F_2 \end{array} - X - L - X \right) \tag{i}$$

wherein $Rf_1$ represents a perfluoroalkylene group; each of $Rf_2$ and $Rf_3$ independently represents a fluorine atom, a perfluoroalkyl group or a perfluoroalkoxy group; at least two among $Rf_1$, $Rf_2$ and $Rf_3$ may bond to each other to form a ring structure; X represents an oxygen atom or a sulfur atom; and L represents a divalent organic group.

9 Claims, No Drawings

FLUORINE-CONTAINING POLYMER AND METHOD OF PRODUCING FLUORINE-CONTAINING POLYMER

TECHNICAL FIELD

The present invention relates to a method of producing a fluorine-containing polymer and a novel fluorine-containing polymer.

BACKGROUND ART

Fluorine-containing polymers may be expected to provide various properties such as weather resistance, heat resistance, chemical resistance, low refractive property, low dielectric property, water- and oil-repellency, and lubricity. These properties are derived from fluorine atoms. Generally, the higher the fluorine content in the polymers is, the more the above properties are expected. However, in the case of aliphatic fluorine-containing polymers, adverse effects are also caused, as the fluorine content increases. For example, the solubility to general organic solvents decreases to cause a deteriorated handling property or the intermolecular force decreases to cause a deteriorated adhesion property to other base materials. To solve these problems, in order to arbitrarily adjust the fluorine content or the main chain structure of the polymers to obtain a desired property, a method of producing a more versatile fluorine polymer has been desired.

Methods of producing an aliphatic fluorine-containing polymer having an adjusted fluorine content may include, for example, a method of copolymerizing of a fluorine-containing olefin (e.g., tetrafluoroethylene, hexafluoropropylene, and perfluorovinyl ether) and vinyl ether; and a method of polymerizing of fluorine-containing acrylate. However, in these cases, a property adjustment by the main chain structure of the polymer was difficult. On the other hand, a method has been known in which an addition reaction of a fluorine-containing-terminal diene and a fluorine-containing diol in the presence of alkali is used to synthesize a fluorine-containing ether-series polymer (see, for example, U.S. Pat. No. 3,391,118). In this method, it is considered that the fluorine content and the main chain structure of the polymers can be in principle adjusted in a relatively-wide range when the fluorine-containing diene and the fluorine-containing diol can be obtained. However, the synthesis of the fluorine-containing-terminal diene is not always easy. In addition, in order to reduce the generation of byproducts and to obtain a polyaddition polymer having a high-molecular weight and a high solvent solubility, an addition reaction of an elementary reaction must progress quantitatively. However, the addition reaction of the perfluoro-terminal olefin with alcohol under a basic condition causes elimination of hydrogen fluoride (HF) and thus is not always a clean reaction (see, for example, Journal of Fluorine Chemistry, 26, 457-465 (1984)). Thus, in order to reduce the generation of byproducts, to simply obtain a polymer having a high-molecular weight and a high solvent solubility by an addition reaction of the fluorine-containing-terminal diene with the fluorine-containing diol, and to adjust the fluorine content and the main chain structure of the polymers in a wide range, the structure and the reaction conditions of the fluorine-containing-terminal olefin must be further improved.

DISCLOSURE OF INVENTION

According to the present invention, a method of producing a fluorine-containing polymer can be provided by which the generation of byproducts can be reduced, a polymer having a high-molecular weight and a high solvent solubility can be obtained efficiently, and the fluorine content and the main chain structure of the polymer can be adjusted in a wide range. Also, according to the present invention, a novel fluorine-containing polymer can be provided.

The present invention provides the following means:

(1) A method of producing a fluorine-containing polymer, comprising conducting an addition polymerization of a fluorine-containing compound having 2 or more terminal fluorine-containing vinyl groups each directly bonded to an oxygen atom per molecule, and a compound having 2 or more groups represented by —XH(X represents an oxygen atom or a sulfur atom).

(2) The method of producing a fluorine-containing polymer described in the above item (1), wherein the fluorine-containing compound having 2 or more terminal fluorine-containing vinyl groups each directly bonded to an oxygen atom per molecule is a compound represented by formula (I):

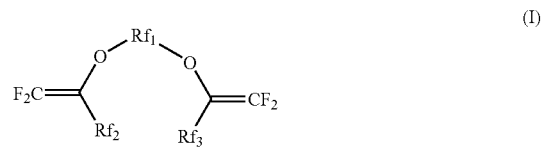

wherein $Rf_1$ represents a perfluoroalkylene group; each of $Rf_2$ and $Rf_3$ independently represents a fluorine atom, a perfluoroalkyl group or a perfluoroalkoxy group; and at least two among $Rf_1$, $Rf_2$ and $Rf_3$ may bond to each other to form a ring structure.

(3) The method of producing a fluorine-containing polymer described in the above item (2), wherein the compound represented by formula (I) is a compound represented by formula (II):

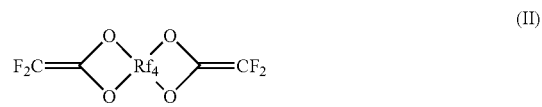

wherein $Rf_4$ represents a tetravalent perfluorinated linking group.

(4) The method of producing a fluorine-containing polymer described in the above item (3), wherein the compound represented by formula (II) is the compound (III) described below.

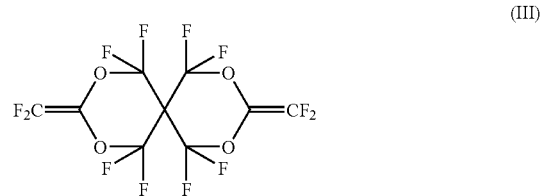

(5) The method of producing a fluorine-containing polymer described in any one of the above items (1) to (4), wherein the compound having 2 or more groups represented by —XH(X represents an oxygen atom or a sulfur atom) is a compound represented by any one of formulas (IV), (V) and (VI):

$$Rf_5(CH_2OH)_n \quad (IV)$$

$$Ar_1-(OH)_n \quad (V)$$

$$HS-R_6-SH \quad (VI)$$

wherein $Rf_5$ represents a perfluoroalkylene group having a valence of "n"; $Ar_1$ represents an arylene group having a valence of "n"; "n" represents an integer of 2 to 6; and $R_6$ represents a divalent alkylene group, arylene group or aralkylene group.

(6) A fluorine-containing polymer comprising a repeating unit represented by formula (i):

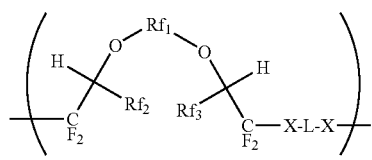
(i)

wherein $Rf_1$ represents a perfluoroalkylene group; each of $Rf_2$ and $Rf_3$ independently represents a fluorine atom, a perfluoroalkyl group or a perfluoroalkoxy group; at least two among $Rf_1$, $Rf_2$ and $Rf_3$ may bond to each other to form a ring structure; X represents an oxygen atom or a sulfur atom; and L represents a divalent organic group.

(7) The fluorine-containing polymer described in the above item (6), wherein the repeating unit represented by formula (i) is a repeating unit represented by formula (ii):

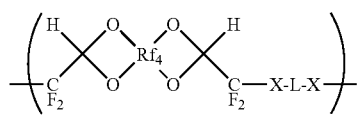
(ii)

wherein $Rf_4$ represents a tetravalent perfluorinated linking group; X represents an oxygen atom or a sulfur atom; and L represents a divalent organic group.

(8) The fluorine-containing polymer described in the above item (7), wherein the repeating unit represented by formula (ii) is a repeating unit represented by formula (iii):

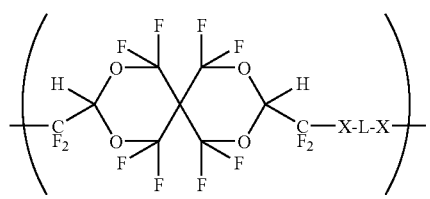
(iii)

wherein X represents an oxygen atom or a sulfur atom; and L represents a divalent organic group.

(9) The fluorine-containing polymer described in any one of the above items (6) to (8),
wherein L is a divalent organic group represented by formula (iv) or (v), and wherein X is an oxygen atom:

(iv)

$$-Ar_1'- \quad (v)$$

wherein $Rf_5'$ represents a divalent perfluoroalkylene group, and $Ar_1'$ represents a divalent arylene group.

(10) The fluorine-containing polymer described in any one of the above items (6) to (8),
wherein L is a divalent organic group represented by formula (vi), and
wherein X is a sulfur atom:

$$-R_6- \quad (vi)$$

Wherein $R_6$ represents a divalent alkylene group, arylene group or aralkylene group Other and further features and advantages of the invention will appear more fully from the following description.

BEST MODE FOR CARRYING OUT INVENTION

The method of producing a fluorine-containing polymer of the present invention can be achieved by conducting an addition polymerization of a fluorine-containing compound having, per molecule, 2 or more terminal fluorine-containing vinyl groups each directly bonded to an oxygen atom, and a compound having 2 or more groups represented by —XH, where X represents an oxygen atom or a sulfur atom.

In a preferred embodiment, the fluorine-containing compound having, per molecule, 2 or more terminal fluorine-containing vinyl groups each directly bonded to an oxygen atom is represented by the following Formula (I):

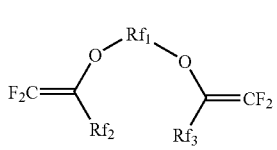
(I)

wherein $Rf_1$ represents a perfluoroalkylene group, each of $Rf_2$ and $Rf_3$ independently represents a fluorine atom, a perfluoroalkyl group or a perfluoroalkoxy group, and at least two among $Rf_1$, $Rf_2$ and $Rf_3$ may bond to each other to form a ring structure.

The perfluoroalkylene group represented by $Rf_1$ is preferably a perfluoroalkylene group having 1 to 30 carbon atoms, which may be linear, branched or cyclic, and which may have an ether bond in the chain. The perfluoroalkylene group has more preferably 1 to 20 carbon atoms, and still more preferably 2 to 10 carbon atoms.

The perfluoroalkyl group represented by $Rf_2$ and $Rf_3$ is preferably a perfluoroalkyl group having 1 to 30 carbon atoms, which may be linear, branched or cyclic, and which may have an ether bond in the chain. The perfluoroalkyl group has more preferably 1 to 20 carbon atoms, and still more preferably 1 to 10 carbon atoms.

The perfluoroalkoxy group represented by $Rf_2$ and $Rf_3$ is preferably a perfluoroalkoxy group having 1 to 30 carbon atoms, which may be linear, branched or cyclic, and which may have an ether bond in the chain. The perfluoroalkoxy group has more preferably 1 to 20 carbon atoms, and still more preferably 1 to 10 carbon atoms.

In Formula (I), it is preferred that both of $Rf_2$ and $Rf_3$ be a fluorine atom or a perfluoroalkoxy group. When $Rf_2$ and $Rf_3$ are both a perfluoroalkoxy group, the compound represented by formula (I) is more preferably a compound represented by the following Formula (II).

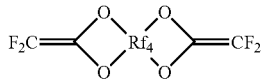
(II)

In Formula (II), $Rf_4$ represents a tetravalent perfluorinated linking group. The tetravalent perfluorinated linking group represented by $Rf_4$ is preferably a perfluoroalkylene group having 1 to 30 carbon atoms, which may be linear, branched or cyclic, and which may have an ether bond in the chain. The perfluoroalkylene group has more preferably 4 to 20 carbon atoms, and still more preferably 5 to 10 carbon atoms.

Specific examples of the compound represented by Formula (I) or (II) will be shown below, but the present invention is not limited thereto.

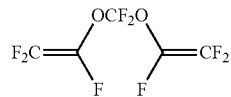
(I-1)

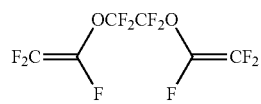
(I-2)

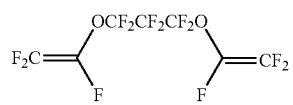
(I-3)

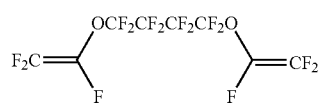
(I-4)

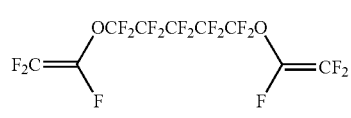
(I-5)

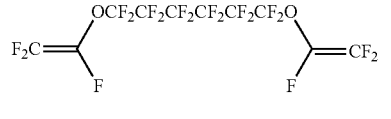
(I-6)

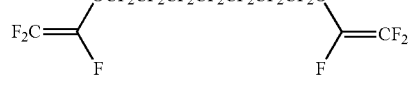
(I-7)

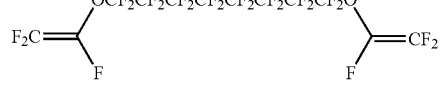
(I-8)

(I-9)

-continued

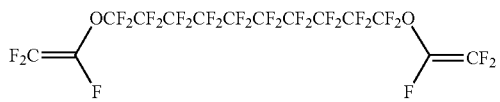
(I-10)

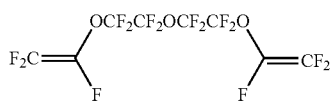
(I-11)

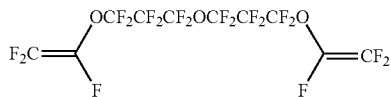
(I-12)

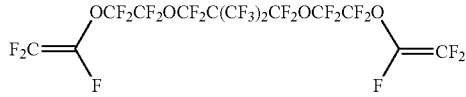
(I-13)

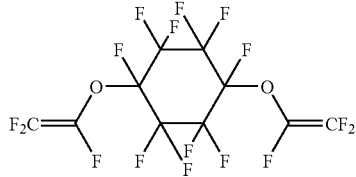
(I-14)

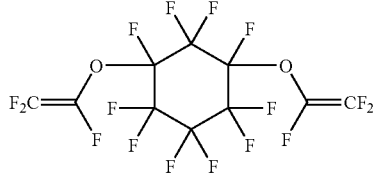
(I-15)

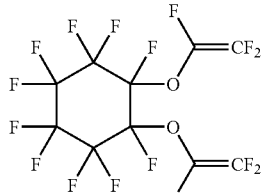
(I-16)

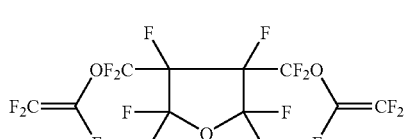
(I-17)

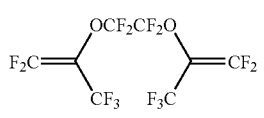
(I-18)

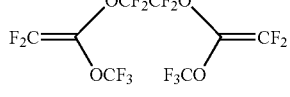
(I-19)

(I-20)

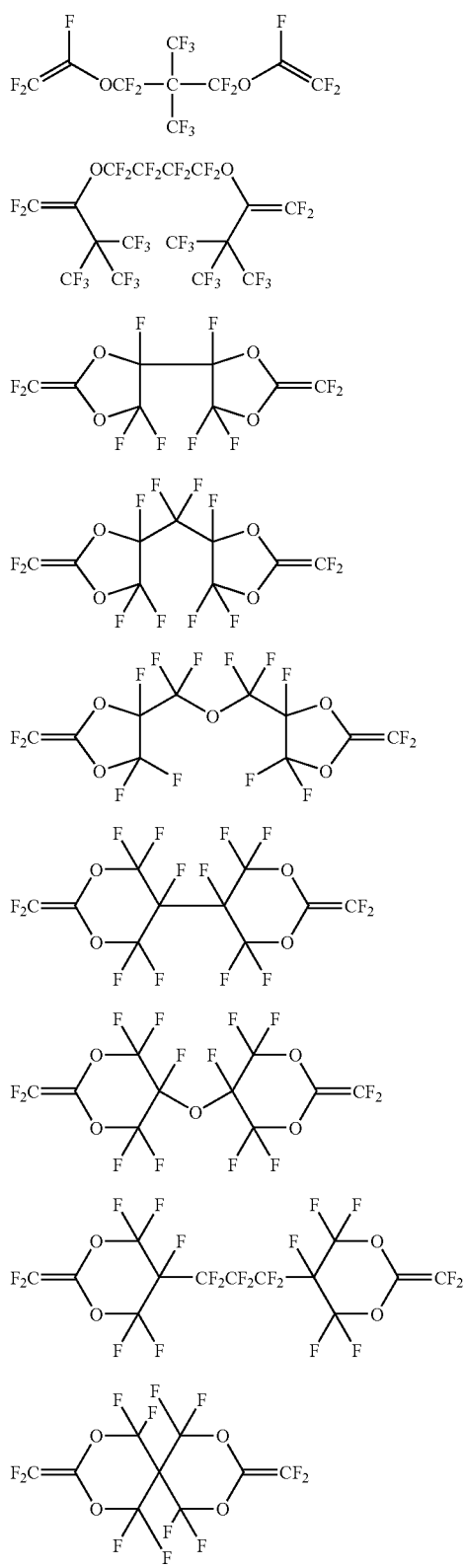

The compound having 2 or more groups represented by —XH (where X represents an oxygen atom or a sulfur atom) for use in the method of producing a fluorine-containing polymer of the present invention is preferably a polyol having 2 or more hydroxyl groups per molecule or a polythiol having 2 or more mercapto groups per molecule, and is more preferably a compound represented by any one of the following Formulas (IV), (V) and (VI):

$$Rf_5(CH_2OH)_n \qquad (IV)$$

$$Ar_1-(OH)_n \qquad (V)$$

$$HS-R_6-SH \qquad (VI)$$

wherein $Rf_5$ represents a perfluoroalkylene group having a valence of "n"; $Ar_1$ represents an arylene group having a valence of "n"; "n" represents an integer of 2 to 6; and $R_6$ represents a divalent alkylene group, arylene group or aralkylene group.

The perfluoroalkylene group represented by $Rf_5$ having a valence of "n" is preferably a perfluoroalkylene group having 1 to 30 carbon atoms, which may be linear, branched or cyclic, and which may have an ether bond in the chain. The perfluoroalkylene group has more preferably 1 to 20 carbon atoms, and still more preferably 2 to 10 carbon atoms.

The arylene group represented by $Ar_1$ having a valence of "n" is preferably a substituted or unsubstituted arylene group having 6 to 30 carbon atoms. The arylene group has more preferably 6 to 20 carbon atoms, and still more preferably 6 to 10 carbon atoms.

Examples of the substituent of the arylene group include halogen atoms (for example, a fluorine atom, a chlorine atom, a bromine atom, and an iodine atom), alkyl groups having 20 or less carbon atoms (for example, methyl or ethyl), aryl groups having 30 or less carbon atoms (for example, phenyl or naphtyl), a cyano group, a carboxyl group, alkoxycarbonyl groups having 20 or less carbon atoms (for example, methoxycarbonyl), aryloxycarbonyl groups having 30 or less carbon atoms (for example, phenoxycarbonyl), carbamoyl groups (for example, a carbamoyl group, N-phenylcarbamoyl group, N,N-dimethylcarbamoyl group), alkycarbonyl groups having 20 or less carbon atoms (for example, acetyl), arylcarbonyl groups having 30 or less carbon atoms (for example, benzoyl), nitro group, amino groups (for example, amino, dimethylamino, anilino), acylamino groups having 20 or less carbon atoms (for example, acetoamino and ethoxycarbonylamino), sulfonamido groups (for example, methanesulfonamido), imido groups (for example, succinimido and phthalimido), imino groups (for example, benzylideneimino), a hydroxy group, alkoxy groups having 20 or less carbon atoms (for example, methoxy), aryloxy groups having 30 or less carbon atoms (for example, phenoxy), acyloxy groups having 20 or less carbon atoms (for example, acetoxy), alkylsulfonyloxy groups having 20 or less carbon atoms (for example, methanesulfonyloxy), arylsulfonyloxy groups having 30 or less carbon atoms (for example, benzenesulfonyloxy), sulfo groups, sulfamoyl groups (for example, sulfamoyl and N-phenylsulfamoyl), alkylthio groups having 20 or less carbon atoms (for example, methylthio), arylthio groups having 30 or less carbon atoms (for example, phenylthio), alkylsulfonyl groups having 20 or less carbon atoms (for example, methanesulfonyl), arylsulfonyl groups having 30 or less carbon atoms (for example, benzenesulfonyl), and heterocyclic groups. The substituent may be further substituted. When plural substituents are present, they may be the same or different. Further, these substituents may be combined with each other to form a ring.

"n" is preferably 2 or 3, more preferably 2.

The divalent alkylene group, arylene group or alkylene group represented by $R_6$ may include a divalent linking group, such as an ether bond, a thioether bond, and a sulfonyl group.

The divalent alkylene group represented by $R_6$ is preferably an alkylene group having 1 to 30 carbon atoms, which may be linear, branched or cyclic. The alkylene group has more preferably 1 to 20 carbon atoms, and still more preferably 1 to 10 carbon atoms.

The divalent arylene group represented by $R_6$ is preferably a substituted or unsubstituted arylene group having 6 to 30 carbon atoms. The divalent arylene group has more preferably 6 to 20 carbon atoms, and still more preferably 6 to 10 carbon atoms.

The divalent aralkylene group represented by $R_6$ is preferably a substituted or unsubstituted aralkylene group having 7 to 30 carbon atoms. The aralkylene group has more preferably 7 to 20 carbon atoms, and still more preferably 7 to 10 carbon atoms.

The substituent group of the divalent alkylene group, arylene group or aralkylene group represented by $R_6$ may be the same one as the examples of the substituent of the arylene group represented by $Ar_1$.

Preferable examples of the compound having 2 or more groups represented by —XH (where X represents an oxygen atom or a sulfur atom) are shown below, but the compounds that can be used in the present invention are not limited to the following specific examples.

HOCH₂CF₂CH₂OH (IV-1)

HOCH₂CF₂CF₂CH₂OH (IV-2)

HOCH₂CF₂CF₂CF₂CH₂OH (IV-3)

HOCH₂CF₂CF₂CF₂CF₂CH₂OH (IV-4)

HOCH₂CF₂CF₂CF₂CF₂CF₂CH₂OH (IV-5)

HOCH₂CF₂CF₂CF₂CF₂CF₂CF₂CH₂OH (IV-6)

HOCH₂CF₂CF₂CF₂CF₂CF₂CF₂CF₂CH₂OH (IV-7)

HOCH₂CF₂CF₂CF₂CF₂CF₂CF₂CF₂CF₂CH₂OH (IV-8)

HOCH₂CF₂CF₂CF₂CF₂CF₂CF₂CF₂CF₂CF₂CF₂CF₂CH₂OH (IV-9)

HOCH₂CF₂OCF₂CH₂OH (IV-10)

HOCH₂CF₂CF₂OCF₂CF₂CH₂OH (IV-11)

HOCH₂CF₂OCF₂C(CF₃)₂CF₂OCF₂CH₂OH (IV-12)

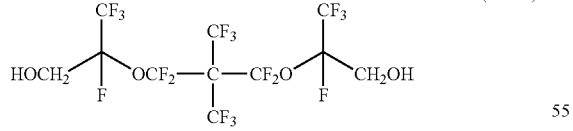
(IV-13)

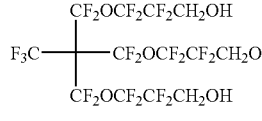
(IV-14)

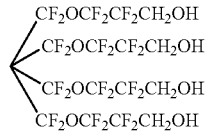
(IV-15)

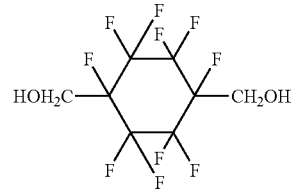
(IV-16)

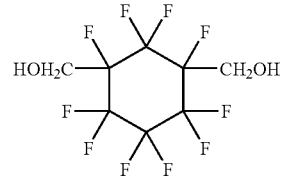
(IV-17)

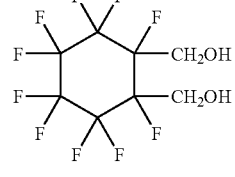
(IV-18)

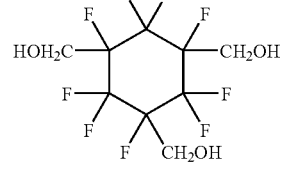
(IV-19)

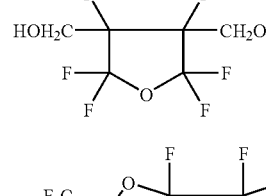
(IV-20)

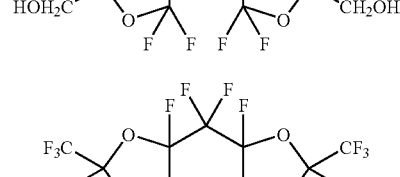
(IV-21)

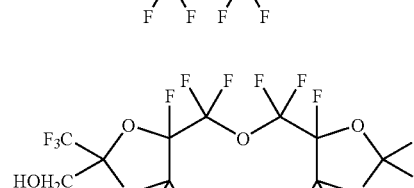
(IV-22)

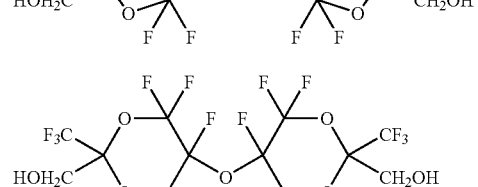
(IV-23)

(IV-24)

(IV-25)
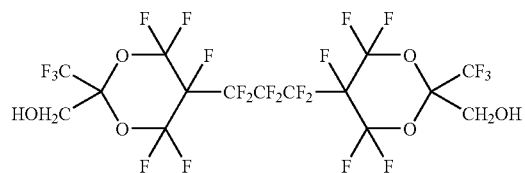
(IV-26)
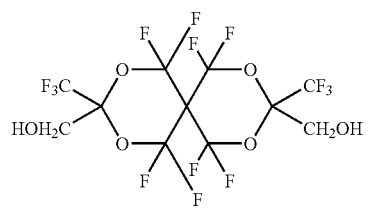
(V-1)
(V-2)
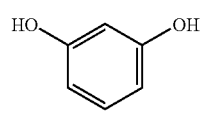
(V-3)
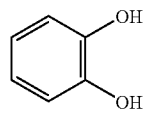
(V-4)
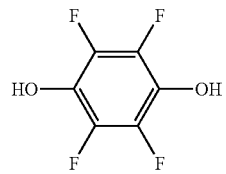
(V-5)
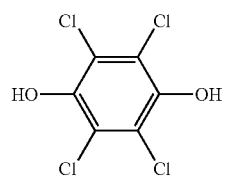
(V-6)
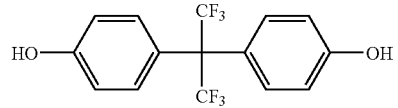
(V-7)
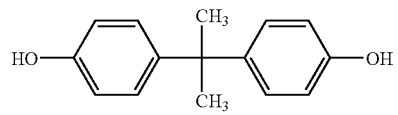
(V-8)
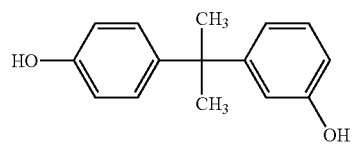
(V-9)
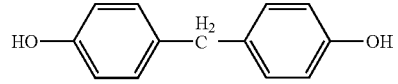
(V-10)
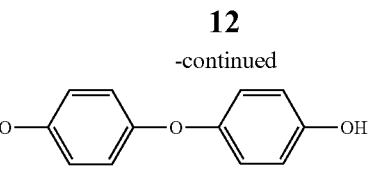
(V-11)
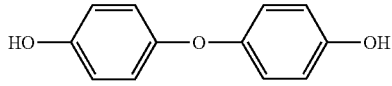
(V-12)
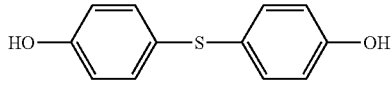
(V-13)
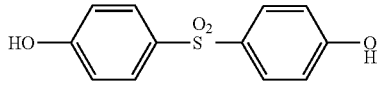
(V-14)
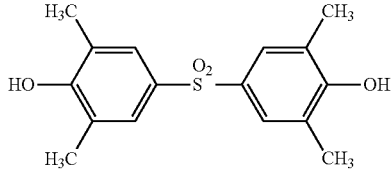
(V-15)
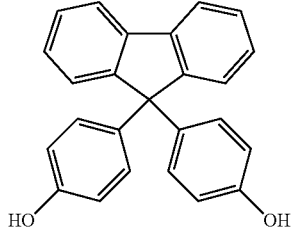
(V-16)
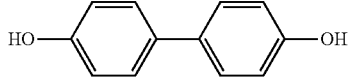
(V-17)
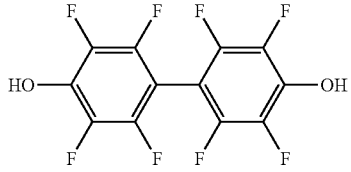
(V-18)
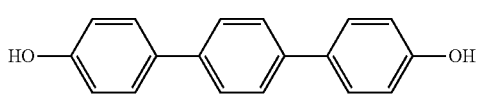
(VI-1)
$HSCH_2CH_2SH$
(VI-2)
$HSCH_2CH_2CH_2SH$
(VI-3)
$HSCH_2CH_2CH_2CH_2SH$
(VI-4)
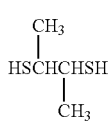
(VI-5)
$HSCH_2CH_2CH_2CH_2CH_2SH$
(VI-6)
$HSCH_2CH_2CH_2CH_2CH_2CH_2SH$
(VI-7)
$HSCH_2CH_2CH_2CH_2CH_2CH_2CH_2SH$

HSCH₂CH₂CH₂CH₂CH₂CH₂CH₂SH (VI-8)

HSCH₂CH₂CH₂CH₂CH₂CH₂CH₂CH₂SH (VI-9)

HSCH₂CH₂OCH₂CH₂SH (VI-10)

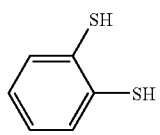
(VI-11)

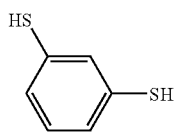
(VI-12)

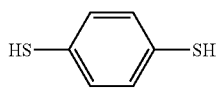
(VI-13)

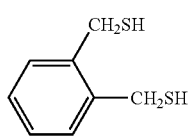
(VI-14)

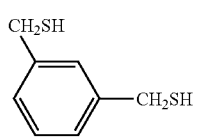
(VI-15)

(VI-16)

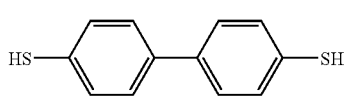
(VI-17)

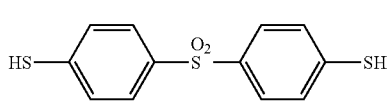
(VI-18)

By the method of producing the fluorine-containing polymer of the present invention, the generation of byproducts can be reduced and a fluorine-containing polymer having a high-molecular weight and a high solvent solubility can be produced efficiently.

The fluorine-containing polymer of the present invention has a repeating unit represented by formula (i), preferably a repeating unit represented by formula (ii), and more preferably a repeating unit represented by formula (iii).

The fluorine-containing polymer of the present invention is preferably obtained by the above method of conducting an addition polymerization of a fluorine-containing compound having, per molecule, 2 or more terminal fluorine-containing vinyl groups each directly bonded to an oxygen atom, and a compound having 2 or more groups represented by —XH, where X represents an oxygen atom or a sulfur atom (e.g., the method described in the above item (1), preferably the method described in any one of the above items (2) to (4)).

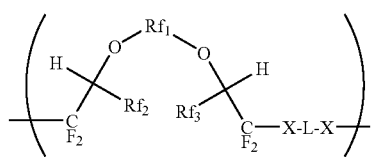
(i)

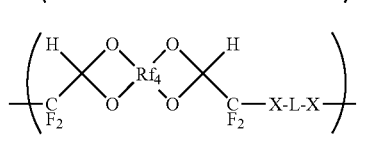
(ii)

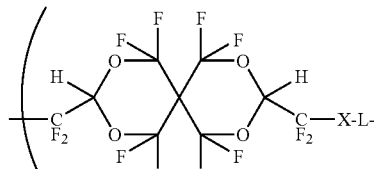
(iii)

In the formulae (i) to (iii), $Rf_1$, $Rf_2$, $Rf_3$, and $Rf_4$ have the same meanings as those of the above ones, the specific examples of which are the same as the groups of the parts corresponding to $Rf_1$, $Rf_2$, $Rf_3$, and $Rf_4$ of the compounds shown as specific examples of the compounds represented by the above formulae (I) and (II).

L represents a divalent linking group. In formula (i), (ii), or (iii), when X is an oxygen atom, L is preferably a divalent organic group represented by formula (iv) or (v).

$$—\overset{H_2}{C}—Rf_5{}'—\overset{H_2}{C}— \quad \text{(iv)}$$

$$—Ar_1{}'— \quad \text{(v)}$$

In formulas (iv) and (v), $Rf_5{}'$ represents a divalent perfluoroalkylene group. The divalent perfluoroalkylene group may be linear, branched or cyclic, and may have an ether bond in the chain. The perfluoroalkylene group has preferably 1 to 30 carbon atoms, more preferably 1 to 20 carbon atoms, and still more preferably 2 to 10 carbon atoms.

$Ar_1{}'$ represents a substituted or unsubstituted, divalent arylene group. The divalent arylene group preferably has 6 to 30 carbon atoms, more preferably 6 to 20 carbon atoms, and still more preferably 6 to 10 carbon atoms. Specific examples of $Rf_5{}'$ and $Ar_1{}'$ are the same as the group of the part corresponding to $Rf_5$ or $Ar_1$ of the compounds shown as specific examples of the compounds represented by the above formula (IV) or (V).

In formula (i), (ii), or (iii), when X is a sulfur atom, L is preferably a divalent organic group represented by formula (vi).

$$—R_6— \quad \text{(vi)}$$

In formula, $R_6$ has the same meaning as that in formula (VI).

The ratio of the repeating unit represented by formula (i) in the fluorine-containing polymer of the present invention is not particularly limited. The molecular weight of the polymer can be set arbitrarily. However, the number of repeating units represented by formula (i) in the fluorine-containing polymers is preferably 2 or more, more preferably 5 to 1,000.

Although the molecular weight of the fluorine-containing polymer of the present invention is not particularly limited, the number-average molecular weight is preferably 500 to 1,000,000, more preferably 5,000 to 100,000.

The terminal group of the fluorine-containing polymer of the present invention is not particularly limited. Examples of the terminal group may be an ordinary terminal group. Examples thereof include a fluorine atom, —XH(X represents an oxygen atom or a sulfur atom) group, an alkoxy group, an aryloxy group, an alkylthio group, an arylthio group, a =CF$_2$ group, an acyl group, an amide group, and a carboxyl group.

In the present invention, a method of synthesizing the compound represented by formula (I) is not particularly limited, and the method includes a series of steps using a liquid-phase fluorination reaction as a key reaction. Details of reaction conditions in respective steps may be set with reference to documents such as JP-T-4-500520 ("JP-T" means a published Japanese translation of PCT international application), International Publications WO 00/56694 A and WO 02/004397 A, JP-T-2003-518051, and documents cited in these documents.

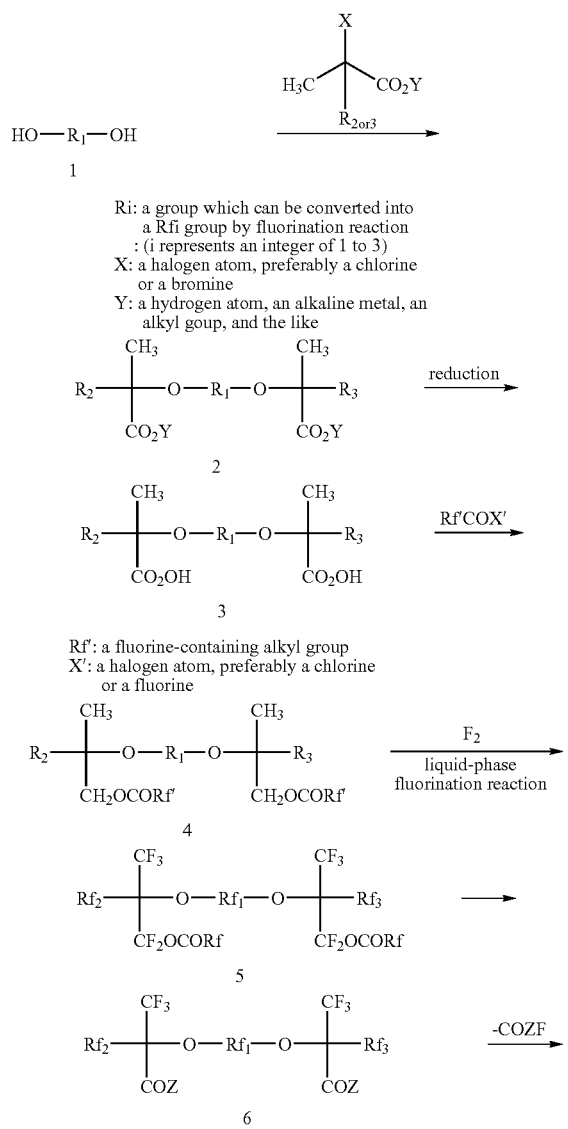

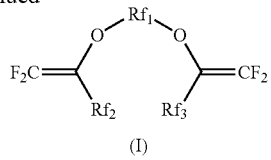

(I)

A variety of commercially available products can be used as the compound having 2 or more —XH groups, where X represents an oxygen atom or a sulfur atom. Additionally, a fluorine-containing alcohol represented by Formula (IV) can also be synthesized by carrying out a liquid-phase fluorination reaction to yield an ester derivative such as the compound in Reaction Scheme 6, and reducing the ester derivative with a hydride using reagents such as LiAlH$_4$ or NaBH$_4$.

The fluorine-containing polymers according to the present invention can be obtained through the step of carrying out an addition polymerization of a suitable combination of a fluorine-containing compound having, per molecule, 2 or more terminal fluorine-containing vinyl groups each directly bonded to an oxygen atom, with a compound having 2 or more —XH groups, wherein X represents an oxygen atom or a sulfur atom. The addition polymerization reaction may be conducted in the absence of a catalyst, but is preferably conducted in the presence of a catalyst effective for promoting the reaction. Examples of the catalyst effective for promoting the reaction include basic catalysts and metallic catalysts.

Examples of preferable basic catalysts include: inorganic bases such as alkali metal hydroxide (for example, lithium hydroxide, sodium hydroxide, potassium hydroxide, and cesium hydroxide), alkali earth metal hydroxide (for example, magnesium hydroxide, calcium hydroxide, strontium hydroxide, and barium hydroxide), alkali metal carbonate (for example, lithium carbonate, sodium carbonate, potassium carbonate, and cesium carbonate), alkali earth metal carbonate (for example, magnesium carbonate, calcium carbonate, strontium carbonate, and barium carbonate), alkali metal hydrogencarbonate (for example, lithium hydrogencarbonate, sodium hydrogencarbonate, potassium hydrogencarbonate, and cesium hydrogencarbonate), and alkali earth metal hydrogencarbonate (for example, magnesium hydrogencarbonate, calcium hydrogencarbonate, strontium hydrogencarbonate, and barium hydrogencarbonate); and organic bases such as pyridine, picoline, lutidine, collidine, triethylamine, diisopropyl ethylamine, 1,8-diazabicyclo[5.4.0]undecene, and 1,4-diazabicyclo[2.2.2]octane. Examples of more preferable bases include sodium hydroxide, potassium hydroxide, sodium carbonate, potassium carbonate, triethylamine, diisopropyl ethylamine, 1,8-diazabicyclo[5.4.0]undecene, and 1,4-biazabicyclo[2.2.2]octane.

The amount of the base is preferably 0.1 equivalent to 10 equivalent, and more preferably 0.5 equivalent to 5 equivalent, to the group —XH to be reacted.

Examples of preferred metallic catalysts include Group 10 transition metallic catalysts/ligands as described, for example, in Angew. Chem. Int. Ed. 2005, 44, 1128 and JP-A-2006-199625. The amount of the transition metal is preferably 0.005 equivalent to 1 equivalent, and more preferably 0.01 equivalent to 0.1 equivalent, to the group —XH to be reacted.

The addition polymerization of the fluorine-containing compound having, per molecule, 2 or more terminal fluorine-containing vinyl groups each directly bonded to an oxygen atom and the compound having 2 or more —XH groups, wherein X represents an oxygen atom or a sulfur atom may be performed in a solvent or without a solvent. Examples of preferable solvent include: general organic solvents such as dichloromethane, chloroform, carbon tetrachloride, diethyl ether, dibutyl ether, cyclopentylmethyl ether, diglyme, tetrahydrofuran, dioxane, acetone, ethyl acetate, butyl acetate, methyl ethyl ketone, cyclohexanone, hexane, heptane, toluene, xylene, acetonitrile, N,N-dimethylformamide, N,N-dimethylacetoamide, 1-methylpyrrolidone, 1,3-dimethyl-2-imidazolidinone, and dimethylsulfoxide; fluorine-containing solvents such as AK-225 (registered trademark, manufactured by ASAHI GLASS CO., LTD), 2,2,2-trifluoroethylmethyl ether, 2,2,2-trifluoroethyldifluoromethyl ether, 2,2,3,3,3-pentafluoropropylmethyl ether, 2,2,3,3,3-pentafluoropropyldifluoromethyl ether, 2,2,3,3,3-pentafluoropropyl-1,1,2,2-tetrafluoroethyl ether, 1,1,2,2-tetrafluoroethylmethyl ether, 1,1,2,2-tetrafluoroethylethyl ether, 1,1,2,2-tetrafluoroethyl-2,2,2-trifluoroethyl ether, 2,2,3,3-tetrafluoropropyldifluoromethyl ether, 1,1,2,2-tetrafluoroethyl-2,2,3,3-tetrafluoropropyl ether, hexafluoroisopropylmethyl ether, 1,1,3,3,3-pentafluoro-2-trifluoromethylpropylmethyl ether, 1,1,2,3,3,3-hexafluoropropylmethyl ether, 1,1,2,3,3,3-hexafluoropropylethyl ether, 2,2,3,4,4,4-hexafluorobutyldifluoromethyl ether, fluorobenzene, 1,2-difluorobenzene, 1,3-difluorobenzene, 1,4-difluorobenzene, 2,4-difluorotoluene, 2,6-difluorotoluene, 3,4-difluorotoluene, 1,2,3-trifluorobenzene, 1,2,4-trifluorobenzene, 1,3,5-trifluorobenzene, 2,3,4-trifluorotoluene, 1,2,3,4-tetrafluorobenzene, 1,2,3,5-tetrafluorobenzene, 1,2,4,5-tetrafluorobenzene, pentafluorobenzene, hexafluorobenzene, α,α,α-trifluoromethylbenzene, 1,3-bis(trifluoromethyl)benzene, and 1,4-bis(trifluoromethyl)benzene; and perfluoro solvents such as a perfluoroalkane compound (FC-72 (trade name, manufactured by Sumitomo 3M Limited) or the like), a perfluoroether compound (FC-75, FC-77 (both of which are trade name, manufactured by Sumitomo 3M Limited) or the like), a perfluoropolyether compound (trade name: Krytox (registered trademark, manufactured by Du Pont Kabushiki Kaisha), Fomblin (registered trademark, manufactured by AUSIMONT), Galden (registered trademark, manufactured by AUSIMONT), DEMNUM (manufactured by DAIKIN INDUSTRIES, Ltd.), or the like), a chlorofluorocarbon compound (CFC-11, CFC-113, or the like), a chlorofluoropolyether compound, a perfluorotrialkylamine compound, an inactivated fluid (trade name: Fluorinert (registered trade name, manufactured by Sumitomo 3M Limited)); water; and mixture thereof.

The amount of the solvent is preferably 0.1 time to 100 times, more preferably 1 time to 50 times, and further preferably 2 times to 20 times the weight of the monomers.

The reaction may be conducted in a two-phase system. In this case, the catalyst is preferably a phase-transfer catalyst that can transfer between the two phases. Examples of such phase-transfer catalysts usable in a two-phase system containing water and an organic solvent include quaternary ammonium salts such as benzyltributylammonium bromide, tetrabutylammonium chloride, and tetrabutylammonium bromide; and quaternary phosphonium salts such as tetrabutylphosphonium bromide and hexadecyltributylphosphonium bromide.

The equivalent ratio of 2 monomers (the number of olefins involved in the addition reaction/the number of —XH groups) can be variously adjusted according to the purpose. However, in order to obtain a polymer having a high-molecular weight as much as possible, the equivalent ratio is preferably close to 1 as much as possible. In the present invention, the equivalent ratio of the fluorine-containing compound having, per molecule, 2 or more terminal fluorine-containing vinyl groups each directly bonded to an oxygen atom to the compound having 2 or more groups represented by —XH (where X represents an oxygen atom or a sulfur atom) is preferably 0.5 to 2.0, more preferably 0.8 to 1.2. When the molecular weight of the polymer is maximized, the equivalent ratio is preferably 0.99 to 1.01.

The reaction temperature is preferably −20° C. to 150° C., more preferably 0° C. to 100° C., and still more preferably 20° C. to 80° C.

The reaction time may vary depending on the types and amounts of the catalyst, substrates and solvent to be used, the reaction temperature, and the stirring efficiency. While controlling these parameters, the reaction is preferably conducted for 10 minutes to 96 hours, more preferably for 30 minutes to 48 hours, and still more preferably for 1 hour to 24 hours.

According to the present invention, the generation of byproducts can be reduced, and a fluorine-containing polymer having a high-molecular weight and a high solvent solubility can be obtained efficiently and simply by the addition polymerization. Furthermore, the fluorine content and the main chain structure can be adjusted in a wide range, and, depending on an application, a polymer having desired properties specific to fluorine such as weather resistance, heat resistance, chemical resistance, low refractive property, low dielectric property, water- and oil-repellency, and lubricity, can be produced easily.

The present invention will be described in more detail based on the following examples, but the present invention is not limited thereto.

EXAMPLES

Reference Example

Synthesis of Materials

The perfluorodiene (III) and the fluorine-containing diol (IV-24) were synthesized according to the following schemes:

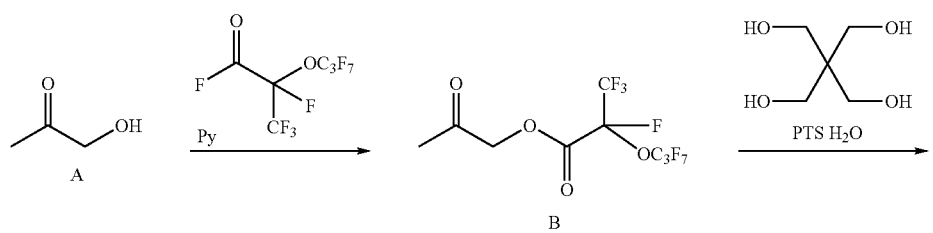

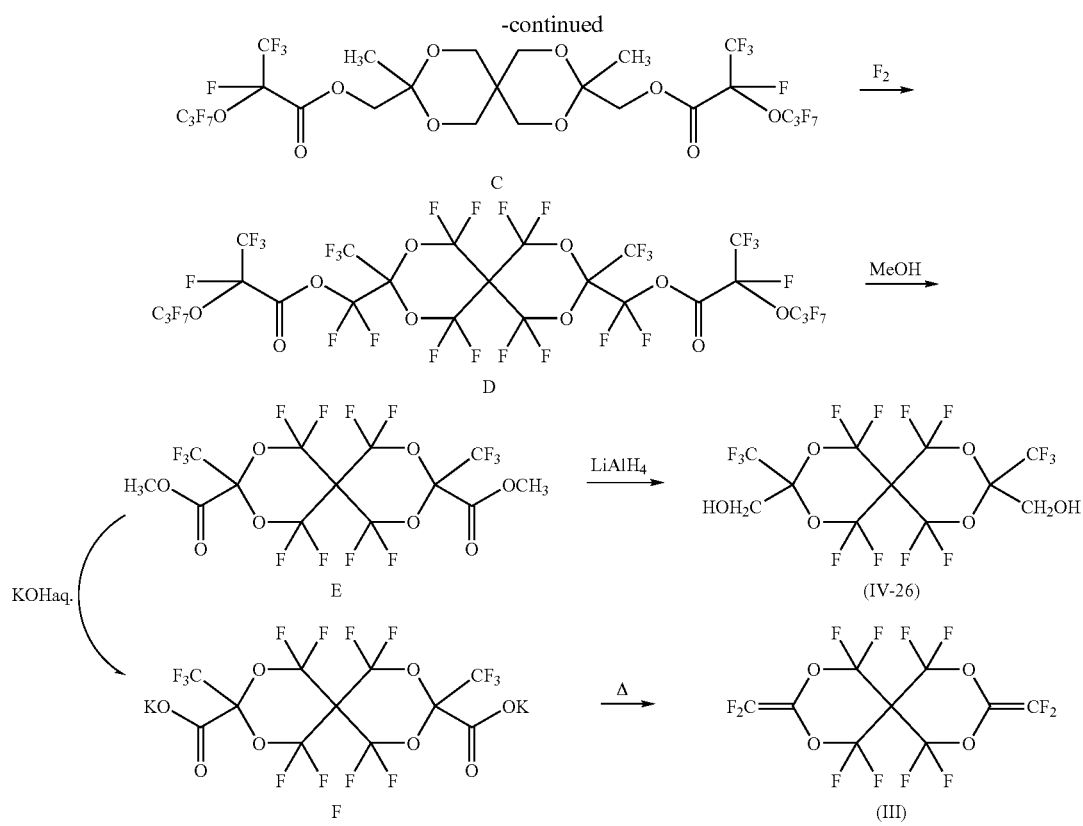

Synthesis of Compound B

To a solution of hydroxyacetone (A, 7.4 g) and pyridine (8.1 ml) in ethyl acetate (100 ml), undecafluoro-(2-methyl-3-oxahexanoic acid)fluoride (10 g) was added dropwise at room temperature (25° C.). After stirring at room temperature for 2 hours, the reaction mixture was poured into diluted hydrochloric acid. After separation, the organic layer was washed with water and a saturated sodium chloride solution and dried with magnesium sulfate. The concentrated residue was purified by column chromatography (eluent: ethyl acetate/hexane), to obtain Compound B (10.2 g, yield: 88%).

$^1$H NMR (CDCl$_3$) δ 2.22 (s, 3H), 4.85 (d, J=16.2 Hz, 1H), 4.96 (d, J=16.2 Hz, 1H)

$^{19}$F NMR (CDCl$_3$) δ −80.3 (1F), −81.8 (3F), −82.5 (3F), −86.7 (1F), −130.2 (2F), −132.8 (1F)

Synthesis of Compound C

Compound B (9.9 g), pentaerythritol (1.74 g), p-toluenesulfonic acid monohydrate (0.25 g) and toluene (50 ml) were refluxed for 4 hours while conducting dehydration. The reaction mixture was washed with an aqueous sodium hydrogen carbonate solution, water and a saturated sodium chloride solution, and then dried with sodium sulfate. The concentrated residue was purified by column chromatography (eluent: ethyl acetate/hexane), to obtain Compound C (5.9 g, yield: 53%).

$^1$H NMR (CDCl$_3$) δ 1.41 (s, 3H), 3.64 to 3.85 (m, 4H), 4.31 (d, J=11.1 Hz, 1H), 4.48 (d, J=11.1 Hz, 1H)

$^{19}$F NMR (CDCl$_3$) δ −80.2 (1F), −81.7 (3F), −82.5 (3F), −86.8 (1F), −130.1 (2F), −132.3 (1F)

Synthesis of Compound D

A perfluoro compound (trade name: FC-72, manufactured by Sumitomo 3M Limited) (180 ml) was placed in a 300-ml Teflon® container equipped with a raw material inlet, a fluorine gas inlet, a helium gas inlet and a gas outlet that was connected via a reflux apparatus cooled with dry ice to a fluorine gas trap. Helium gas was introduced, at a flow rate of 50 ml/min, into the container at an inner temperature of 20° C. for 30 minutes. Sequentially, 20% F$_2$/N$_2$ gas was introduced thereinto at a flow rate of 100 ml/min for 30 minutes. Then, while maintaining the fluorine flow rate as above, a solution of Compound C (4.25 g) in FC-72 (13.5 ml) was added at a rate of 6.2 ml/hr, then a solution of hexafluorobenzene (1 g) in FC-72 (5 ml) was added at the same rate above. Next, 20% F$_2$/N$_2$ gas was introduced thereinto at a flow rate of 100 ml/min for 30 minutes. The reaction mixture was concentrated under atmospheric pressure, and further concentrated under reduced pressure, to obtain Compound D (5.1 g, crude yield: 88%) as a substantially single product.

$^{19}$F NMR (CDCl$_3$) δ −60.6 to −64.4 (m, 8F), −76.7 (s, 6F), −79.8 to −80.0 (m, 1F), −80.3 to −80.6 (m, 1F), 82.0 (m, 6F), 82.1 (s, 6F), −83.4 to −83.8 (m, 4F), −86.7 (bs, 1F), −86.9 (bs, 1F), −130.2 (s, 4F), −132.0 (s, 1F), −132.1 (s, 1F)

Synthesis of Compound E

The crude Compound D (5.1 g) obtained above was added dropwise to a dispersion of sodium fluoride (10 g) in methanol (200 ml), followed by stirring at room temperature for 3 hours. After removing insoluble materials by filtration, the filtrate was concentrated to about 30 ml and extracted with ethyl acetate from a sodium hydrogen carbonate solution. The organic layer was washed with water and a saturated sodium chloride solution and dried with magnesium sulfate. The concentrated residue was purified by column chromatography (eluent: ethyl acetate/hexane), to obtain Compound E (1.8 g, yield: 78%).

$^1$H NMR (CDCl$_3$) δ 3.99 (s, 3H)

$^{19}$F NMR (CDCl$_3$) δ −62.5 to −63.8 (m, 4F), −69.9 to −71.3 (m, 4F), −81.2 (s, 3F), −81.4 (s, 3F)

Synthesis of Fluorine-containing Diol (IV-26)

To a solution of Compound E (0.28 g) in diethyl ether (10 ml), lithium aluminum hydride (0.038 g) was added at 5° C. After stirring at room temperature for 4 hours, the reaction mixture was gradually added with diluted hydrochloric acid. After the mixture was extracted with ethyl acetate, the organic layer was washed with water and a saturated sodium chloride solution, and dried with magnesium sulfate. The concentrated residue was purified by column chromatography (eluent: ethyl acetate/hexane), to obtain Compound (IV-26) (0.2 g, yield: 80%).

$^1$H NMR (CDCl$_3$) δ 2.20 (bs, 1H), 4.21 (bs, 2H)

$^{19}$F NMR (CDCl$_3$) δ −56.2 to −58.6 (m, 4F), −66.0 to −67.3 (m, 4F), 80.9 to 81.0 (m, 6F)

Synthesis of Perfluorodiene (III)

To a solution of Compound E (16.2 g) in methanol (200 ml) and water (40 ml), 10 ml of an 8 N aqueous potassium hydroxide solution was added dropwise at room temperature. The reaction mixture was stirred at room temperature for 2 hours, and the solvent was distilled off under reduced pressure. The concentrated residue was added with 30 ml of water, and further added dropwise with concentrated hydrochloric acid until the mixture became acidic on a pH indicator paper. The precipitated white crystals were filtered, dispersed in water (30 ml), and added dropwise with a 1 N aqueous potassium hydroxide solution to thereby adjust pH to 8. The reaction mixture was concentrated under reduced pressure, the residue was thoroughly dried at 100° C. using a vacuum pump, to obtain Compound F (16.5 g, 93%). The obtained Compound F (2 g) was thermally decomposed at 280° C. under reduced pressure (4 mmHg), and volatile components were collected in a −78° C. trap. The collected liquids were distilled under reduced pressure, and thereby yielded Compound (III) (0.98 g, yield: 74%, GC (gas chromatography) purity of 95%). An analysis of the obtained impurity showed that the impurity was the following proton material (III'). By a processing by lithium hexamethyldisilazide in ether, the compound (III) having a GC purity of 99% or more was obtained.

$^{19}$F NMR (CDCl$_3$) δ −70.7 (s, 8F), −111.2 (s, 4F), b.p. 55° C. (20 mmHg)

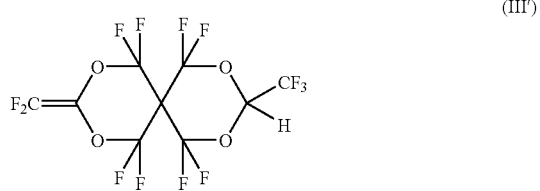

(III')

Example 1

Polymerization of Perfluorodiene (III) and Fluorine-containing Diol (IV-26)

A solution of the Perfluorodiene (III) (1.12 g, GC purity of 95%), Fluorine-containing Diol (IV-26) (1.34 g), tetrabutylammonium bromide (0.18 g), acetonitrile (1 ml), α,α,α-trifluoromethylbenzene (10 ml) and potassium hydroxide (0.32 g) in water (10 ml) was stirred at 50° C. for 41 hours. After cooling to room temperature, the mixture was separated. The organic layer was washed with water and a saturated sodium chloride solution, dried with magnesium sulfate, and concentrated under reduced pressure. The concentrated residue (2.1 g) was dissolved in acetone (2 ml), reprecipitated with chloroform (300 ml), and dried, to obtain 0.5 g of white crystals. The obtained crystals were dissolved in deuterated acetone and subjected to analyses by $^1$H-NMR and $^{19}$F-NMR, to find that the crystals were a linear polymer having the following repeating unit and containing no unsaturated bond formed by elimination of HF.

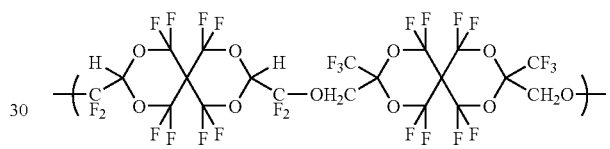

$^1$H NMR (CD$_3$COCD$_3$) δ a: 4.90 (bs), b: 6.44 (bs) a/b=about 2/1

$^{19}$F NMR (CD$_3$COCD$_3$) δ c: −57.62 to −58.94 (m), d: −67.27 to −68.90 (m), e: −71.81 to −73.35 (m), f: −81.50 (s), g: −81.74 (s), h: −88.67 (s) c/d/e/(f+g)/h=about 2/4/2/3/2

A GPC analysis revealed that this polymer had the number-average molecular weight in terms of styrene of 11,500 and the weight-average molecular weight in terms of styrene of 15,800. A temperature at which a 10% mass decrease was caused was 380° C., showing a favorable thermal stability.

Example 2

Polymerization of Perfluorodiene (III) and Fluorine-containing Diol (IV-2)

Perfluoro diene (III) (0.80 g, GC purity 95%), the fluorine-containing diol (IV-24) (0.32 g), and potassium carbonate (0.61 g) were stirred in acetonitrile (10 ml) at a room temperature for 64 hours. The reaction liquid was poured into ethyl acetate (30 ml)/water (30 ml), to separate organic layer. The organic layer was washed with water and a saturated sodium chloride solution, dried with magnesium sulfate, and concentrated under a reduced pressure. By drying the concentrated residue, 1.10 g of an amorphous polymer was obtained. The obtained polymer was dissolved in deuterated acetone and subjected to analyses by $^1$H-NMR and $^{19}$F-NMR, to find that the polymer was a linear polymer having the following repeating unit and containing no unsaturated bond formed by elimination of HF.

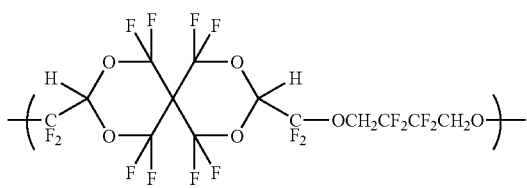

$^1$H NMR (CD$_3$COCD$_3$) δ a: 4.73 (t, J=13.5 Hz), b:6.41 (bs) a/b=about 2/1
$^{19}$F NMR (CD$_3$COCD$_3$) δ c: −67.90 to −68.88 (m), d: −71.63 to −73.30 (m), e: −88.72 (s), f: −88.82 (s), g: −122.70 (t, J=13.5 Hz) c/d/(e+g)/f=about 1/1/1/1

A GPC analysis revealed that this polymer had a number average molecular weight in terms of styrene of 15,000 and a weight average molecular weight in terms of styrene of 37,200. The polymer showed a low refractive index of 1.36.

Example 3

Polymerization of Perfluorodiene (III) and Fluorine-containing Diol (IV-2)

Perfluoro diene (III) (8.10 g, GC purity of more than 99%), the fluorine-containing diol (IV-24) (3.31 g), and potassium carbonate (6.05 g) were stirred in acetonitrile (100 ml) at a room temperature for 72 hours. The reaction liquid was poured into ethyl acetate (500 ml)/water (500 ml), to separate organic layer. The organic layer was washed with water and a saturated sodium chloride solution, dried with magnesium sulfate, and concentrated under a reduced pressure. The concentrated residue (11.40 g) was dissolved in acetone and was reprecipitated from chloroform, thereby obtaining an amorphous polymer (7.85 g). The obtained polymer was dissolved in deuterated acetone and subjected to analyses by $^1$H-NMR and $^{19}$F-NMR, to find that the polymer was a linear polymer having the same repeating unit as in Example 2 and containing no unsaturated bond formed by elimination of HF.

According to the result of the GPC measurement, it was found that this polymer had the number-average molecular weight in terms of styrene of 34,500 and the weight-average molecular weight in terms of styrene of 87,700. A methyl ethyl ketone solution of 0.5 mass % of the resultant polymer in an amount of 40 μl was spin-coated over a 2.5 cm×2.5 cm glass plate (2000 rpm×20 s), the result of which showed a water repellency (a contact angle (water) of 94°). The temperature at which a 10% mass decrease was caused was 420° C., showing a favorable thermal stability.

Example 4

Polymerization of Perfluorodiene (I-4) and Fluorine-containing Diol (IV-2)

Perfluoro diene (I-4) (0.79 g, GC purity 95%), the fluorine-containing diol (IV-2) (0.32 g), and potassium carbonate (0.61 g) were stirred in acetonitrile (10 ml) at a room temperature for 48 hours. The reaction liquid was poured into ethyl acetate (30 ml)/water (30 ml), to separate organic layer. The organic layer was washed with water and a saturated sodium chloride solution, dried with magnesium sulfate, and concentrated under a reduced pressure. By drying the concentrated residue, 1.08 g of an oily polymer was obtained. The obtained polymer was dissolved in deuterated acetone and subjected to analyses by $^1$H-NMR and $^{19}$F-NMR, to find that the polymer was a linear polymer having the following repeating unit and containing no unsaturated bond formed by elimination of HF.

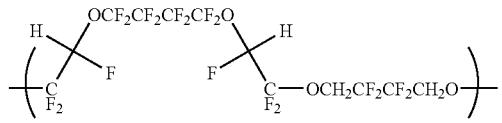

A GPC analysis revealed that this polymer had a number average molecular weight in terms of polystyrene of 14,800.

Example 5

Polymerization of Perfluorodiene (III) and Fluorine-containing Diol (IV-9)

Perfluoro diene (III) (1.0 g, GC purity of more than 99%), the fluorine-containing diol (IV-9) (1.4 g), and potassium carbonate (0.76 g) were stirred in methylethylketone (12.5 ml) at a room temperature for 66 hours. The reaction liquid was poured into ethyl acetate (100 ml)/water (100 ml), to separate organic layer. The organic layer was washed with water and a saturated sodium chloride solution, dried with magnesium sulfate, and concentrated under a reduced pressure. The concentrated residue was dissolved in acetone (10 ml) and was reprecipitated from chloroform, thereby obtaining 1.69 g of an amorphous polymer. The resultant polymer was dissolved in deuterated acetone and subjected to analyses by $^1$H-NMR and $^{19}$F-NMR, to find that the polymer was a linear polymer having the following repeating unit and containing no unsaturated bond formed by elimination of HF.

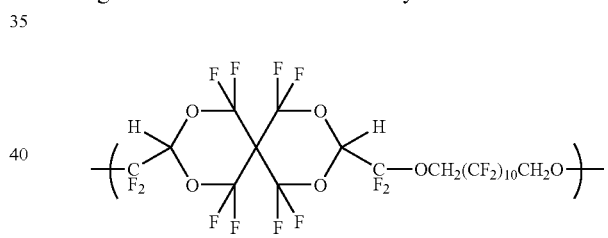

$^1$H NMR (CD$_3$COCD$_3$) δ a: 4.90 (t, J=13.1 Hz), b: 6.42 (bs) a/b=about 2/1
$^{19}$F NMR (CD$_3$COCD$_3$) δ c: −67.90 to −69.02 (m), d: −71.84 to −73.35 (m), e: −88.57 (s), f: −120.42 (s), g: −122.39 (bs), h: −123.61 (s) c/d/e/f/g/h=about 1/1/1/1/3/1

The NMRs showed that the average number of repeating units was about 60. A methyl ethyl ketone solution of 0.5 mass % of the resultant polymer in an amount of 40 μl was spin-coated over a 2.5 cm×2.5 cm glass plate (2000 rpm×20 s), the result of which showed a water repellency (a contact angle (water) of 99°).

Example 6

Polymerization of Perfluorodiene (III) and Fluorine-containing Bisphenol (V-6)

Perfluoro diene (III) (1.0 g, GC purity of more than 99%), the fluorine-containing bisphenol (V-6) (0.84 g), and potassium carbonate (1.1 g) were stirred in methylethylketone (12.5 ml) at a room temperature for 50 hours. The reaction liquid was poured into ethyl acetate (100 ml)/water (100 ml), to separate organic layer. The organic layer was washed with water and a saturated sodium chloride solution, dried with magnesium sulfate, and concentrated under a reduced pressure. The concentrated residue was dissolved in acetone (10 ml) and was reprecipitated from chloroform, thereby obtaining an amorphous polymer (0.91 g). The resultant polymer was dissolved in deuterated acetone and subjected to analyses by $^1$H-NMR and $^{19}$F-NMR. The result demonstrated that the polymer was a linear polymer having the following repeating unit and containing no unsaturated bond formed by elimination of HF.

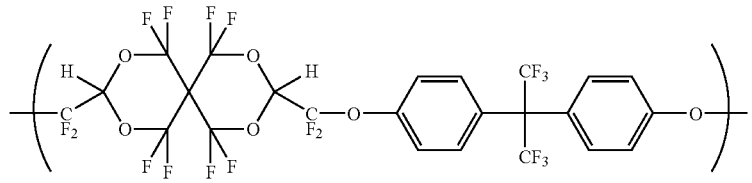

$^1$H NMR (CD$_3$COCD$_3$) δ a: 6.60 (bs), b: 7.49 (d, J=8.25 Hz), c: 7.59 (d, J=8.25 Hz) a/b/c=about 1/2/2

$^{19}$F NMR (CD$_3$COCD$_3$) δ d: −64.55 (s), e: −67.72 to −68.68 (m), f: −71.55 to −73.13 (m), g: −85.21 (bs), h: −85.26 (bs) d/e/f/(g+h)=about 3/2/2/2

According to the result of the GPC measurement, this polymer had the number-average molecular weight in terms of styrene of 22,900 and the weight-average molecular weight in terms of styrene of 52,800. A methyl ethyl ketone solution of 0.5 mass % of the resultant polymer in an amount of 40 μl was spin-coated over a 2.5 cm×2.5 cm glass plate (2000 rpm×20 s), the result of which showed a water repellency (a contact angle (water) of 96°).

Example 7

Polymerization of Perfluorodiene (III) and Dithiol (VI-4)

Perfluorodiene (III) (0.83 g, GC purity of more than 99%), 2,3-butane dithiol (VI-4) (0.24 g), and potassium carbonate (0.63 g) were stirred in methylethylketone (10 ml) at a room temperature for 50 hours. The reaction liquid was poured into ethyl acetate (80 ml)/water (80 ml), to separate organic layer. The organic layer was washed with water and a saturated sodium chloride solution, dried with magnesium sulfate, and concentrated under a reduced pressure. The concentrated residue was dissolved in acetone (5 ml) and was reprecipitated from water, thereby obtaining 0.40 g of an amorphous polymer. The resultant polymer was dissolved in deuterated acetone and subjected to analyses by $^1$H-NMR and $^{19}$F-NMR. The result demonstrated that the polymer was a linear polymer having the following repeating unit.

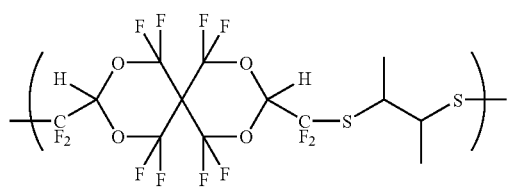

$^1$H NMR (CD$_3$COCD$_3$) δ a: 1.38 (d, J=6.90 Hz), b: 3.81 (q, J=6.90 Hz), c: 6.26 (bs) a/b/c=about 3/1/1

$^{19}$F NMR (CD$_3$COCD$_3$) δ d: −67.48 to −68.39 (m), e: −70.03 to −73.32 (m), f: −87.51 to −89.00 (m) d/e/f=about 1/1/1

According to the result of the GPC measurement, this polymer had the number-average molecular weight in terms of styrene of 12,600 and the weight-average molecular weight in terms of styrene of 20,500. A methyl ethyl ketone solution of 0.5 mass % of the resultant polymer in an amount of 40 μl was spin-coated over a 2.5 cm×2.5 cm glass plate (2000 rpm×20 s), the result of which showed a water repellency (a contact angle (water) of 92°).

Example 8

Polymerization of Perfluorodiene (I-4) and Fluorine-containing Diol (IV-9)

Perfluorodiene (I-4) (0.39 g, GC purity 95%), the fluorine-containing diol (IV-9) (0.56 g), and potassium carbonate (0.41 g) were stirred in methylethylketone (6 ml) at a room temperature for 24 hours. The reaction liquid was poured into ethyl acetate (50 ml)/water (50 ml), to separate organic layer. The organic layer was washed with water and a saturated sodium chloride solution, dried with magnesium sulfate, and concentrated under a reduced pressure. By drying the concentrated residue, 0.93 g of an amorphous polymer was obtained. The obtained polymer was dissolved in deuterated acetone and subjected to analyses by $^1$H-NMR and $^{19}$F-NMR, to find that the polymer was a linear polymer having the following repeating unit and containing no unsaturated bond formed by elimination of HF.

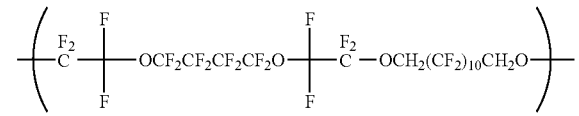

$^1$H NMR (CD$_3$COCD$_3$) δ a: 4.87 (t, J=12.8 Hz), b: 6.85 (d, J=52.2 Hz) a/b=about 2/1

$^{19}$F NMR (CD$_3$COCD$_3$) δ c: −84.89 to −86.15 (m), d: −89.93 to −92.21 (m), e: −120.51 (s), f: −122.44 (s), g: −122.61 (s), h: −123.61, i: −124.03, j: −126.64, k: −146.60 (d, J=52.2 Hz) c/d/e/(f+g)/(h+i)/j/k=about 2/2/2/3/2/2/1

According to the result of the GPC measurement, this polymer had the number-average molecular weight in terms of styrene of 25,800 and the weight-average molecular weight in terms of styrene of 53,100. A methyl ethyl ketone solution of 0.5 mass % of the resultant polymer in an amount of 40 μl was spin-coated over a 2.5 cm×2.5 cm glass plate (2000 rpm×20 s), the result of which showed a water repellency (a contact angle (water) of 93°).

As described above, according to the method of producing a fluorine-containing polymer of the present invention, the generation of byproducts could be reduced and a fluorine-containing polymer having a high-molecular weight and a high solvent solubility could be obtained efficiently and simply. Furthermore, the fluorine content rate and the main chain structure could be adjusted in a wide range.

Industrial Applicability

According to the present invention, the generation of byproducts can be reduced, a fluorine-containing polymer having a high-molecular weight and a high solvent solubility can be obtained simply, and the fluorine content and the main chain structure can be adjusted in a wide range by the addition polymerization of a fluorine-containing compound having 2 or more terminal fluorine-containing vinyl groups each directly bonded to an oxygen atom per molecule, and a compound having 2 or more groups represented by —XH, where X represents an oxygen atom or a sulfur atom. Therefore, according to the present invention, properties specific to fluorine such as a predetermined weather resistance, heat resistance, chemical resistance, low refractive property, low dielectric property, water- and oil-repellency, and lubricity can be easily adjusted.

Having described our invention as related to the present embodiments, it is our intention that the invention not be limited by any of the details of the description, unless otherwise specified, but rather be construed broadly within its spirit and scope as set out in the accompanying claims.

The invention claimed is:

1. A method of producing a fluorine-containing polymer, comprising conducting an addition polymerization of a fluorine-containing compound having 2 or more terminal fluorine-containing vinyl groups each directly bonded to an oxygen atom per molecule, and a compound having 2 or more groups represented by —XH, where X represents an oxygen atom or a sulfur atom, wherein the fluorine-containing compound having 2 or more terminal fluorine-containing vinyl groups each directly bonded to an oxygen atom per molecule is a compound represented by formula (I):

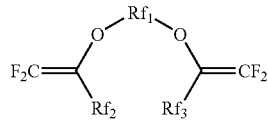

(I)

wherein $Rf_1$ represents a perfluoroalkylene group; each of $Rf_2$ and $Rf_3$ independently represents a fluorine atom, a perfluoroalkyl group or a perfluoroalkoxy group; and at least two among $Rf_1$, $Rf_2$ and $Rf_3$ may bond to each other to form a ring structure.

2. The method of producing a fluorine-containing polymer according to claim 1, wherein the compound represented by formula (I) is a compound represented by formula (II):

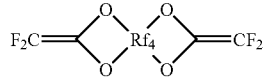

(II)

wherein $Rf_4$ represents a tetravalent perfluorinated linking group.

3. The method of producing a fluorine-containing polymer according to claim 2, wherein the compound represented by formula (II) is the compound (III) described below

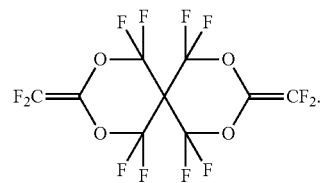

(III)

4. The method of producing a fluorine-containing polymer according to claim 1, wherein the compound having 2 or more groups represented by —XH (where X represents an oxygen atom or a sulfur atom) is a compound represented by any one of formulas (IV), (V) and (VI):

(IV)

(V)

(VI)

wherein $Rf_5$ represents a perfluoroalkylene group having a valence of "n"; $Ar_1$ represents an arylene group having a valence of "n"; "n" represents an integer of 2 to 6; and $R_6$ represents a divalent alkylene group, arylene group or aralkylene group.

5. A fluorine-containing polymer comprising a repeating unit represented by formula (i):

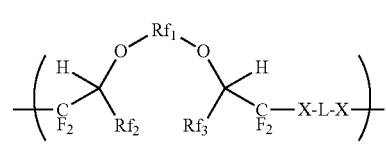

(i)

wherein $Rf_1$ represents a perfluoroalkylene group; each of $Rf_2$ and $Rf_3$ independently represents a fluorine atom, a perfluoroalkyl group or a perfluoroalkoxy group; at least two among $Rf_1$, $Rf_2$ and $Rf_3$ may bond to each other to form a ring structure; X represents an oxygen atom or a sulfur atom; and L represents a divalent organic group.

6. The fluorine-containing polymer according to claim 5, wherein the repeating unit represented by formula (i) is a repeating unit represented by formula (ii):

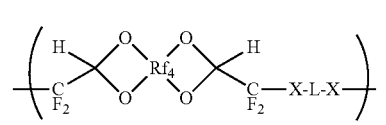

(ii)

wherein $Rf_4$ represents a tetravalent perfluorinated linking group; X represents an oxygen atom or a sulfur atom; and L represents a divalent organic group.

7. The fluorine-containing polymer according to claim 6, wherein the repeating unit represented by formula (ii) is a repeating unit represented by formula (iii):

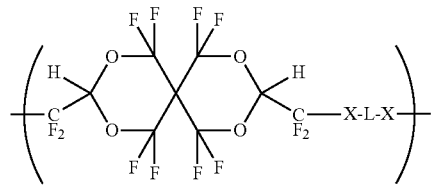

(iii)

wherein X represents an oxygen atom or a sulfur atom; and L represents a divalent organic group.

8. The fluorine-containing polymer according to claim 5, wherein L is a divalent organic group represented by formula (iv) or (v), and wherein X is an oxygen atom:

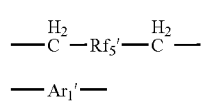

(iv)

—Ar$_1$'— (v)

wherein Rf$_5$' represents a divalent perfluoroalkylene group, and Ar$_1$' represents a divalent arylene group.

9. The fluorine-containing polymer according to claim 5, wherein L is a divalent organic group represented by formula (vi), and wherein X is a sulfur atom:

—R$_6$— (Vi)

wherein R$_6$ represents a divalent alkylene group, arylene group or aralkylene group.

* * * * *